United States Patent [19]

Hoffmann et al.

[11] 4,038,330
[45] July 26, 1977

[54] 1-METHYL-2-HALOGENOMETHYL-3-ISO-PROPENYL-CYCLOPENT-1-ENES

[75] Inventors: Werner Hoffmann, Neuhofen; Karl von Fraunberg, Bobenheim, both of Germany

[73] Assignee: BASF Aktiengesellschaft, Ludwigshafen, Germany

[21] Appl. No.: 665,064

[22] Filed: Mar. 8, 1976

[30] Foreign Application Priority Data

Mar. 29, 1975 Germany .............................. 2513995

[51] Int. Cl.$^2$ ............................................ C07C 23/08
[52] U.S. Cl. .................................................. 260/648 C
[58] Field of Search .................................... 260/648 C

[56] References Cited
U.S. PATENT DOCUMENTS 2,721,160  10/1955  Newcomer ...................... 260/648 C Primary Examiner—D. Horwitz
Attorney, Agent, or Firm—Keil, Thompson & Shurtleff

[57] ABSTRACT

Cyclopentene derivatives of the general formula

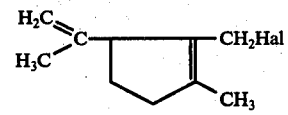

where Hal is chlorine, bromine or iodine.

2 Claims, No Drawings

1-METHYL-2-HALOGENOMETHYL-3-ISOPROPENYL-CYCLOPENT-1-ENES

The present invention relates to cyclopentene derivatives of the general formula I

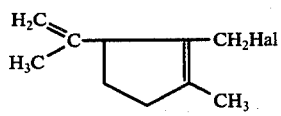   I where Hal is chlorine, bromine or iodine.

It is known that many compounds having a cyclopentene structure are scents (compare, e.g., German Published Application 2,405,568).

It is an object of the present invention to provide new scents of the cyclopentene series.

We have found that this object is achieved by providing the compounds I, which are valuable intermediates for the manufacture of scents of the cyclopentene series.

Further, we have found that the compounds I are obtained economically and in high yields when 1-methyl-2-methylene-3-isopropenyl-cyclopentan-1-ol (II)

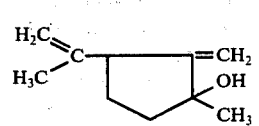   II is reacted with a chlorinating, brominating or iodinating agent at from $-50°$ to $+100°$ C.

The cyclopentanol II used as a starting compound is obtainable, e.g., in accordance with the process of German Pat. No. 1,082,257, by cyclization of dehydrolinalool

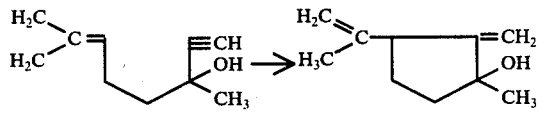

Suitable chlorinating, brominating and iodinating agents are, in general terms, those compounds in which the halogen has a partial negative charge, i.e., for example, hydrogen chloride, hydrogen bromide and acid halides of mineral acids, e.g. phosphorus trichloride, phosphorus pentachloride, thionyl chloride and phosgene and the corresponding bromine compounds. Iodinating agents, e.g. hydrogen iodide, can also be used, but these offer no advantages over the cheaper chlorine and bromine compounds.

It is advantageous gradually to add not more than the stoichiometric amount of the halogenating agent to the alcohol II, so as to suppress an addition reaction of hydrogen halide at the isopropenyl group.

The halogenation can be carried out in the presence or absence of a solvent, but the presence of an inert solvent, e.g. benzene, toluene, pentane, cyclohexane, ether, acetone, methylene chloride or dimethylformamide, is preferred.

If hydrogen halides are used as halogenating agents, the presence of water does not interfere and accordingly it is possible to employ, e.g., aqueous hydrochloric acid.

Depending on the reactivity of the halogenating agent, the reaction is carried out at higher or lower temperatures within the stated temperature range. In general, it is preferred to carry out the reaction at from $-20°$ C to room temperature.

In some cases, the reaction takes place more rapidly if small amounts of a tertiary amine, e.g. pyridine, are present. If a hydrogen halide is used as the halogenating agent, the presence of copper or of copper salts, e.g. copper-I chloride or copper-II acetate, has an accelerating effect.

The halogenating mixtures are worked up in the conventional manner, by first filtering off the solids, separating the organic phase from any aqueous phase which may be present, washing the organic phase first with aqueous sodium carbonate solution and then with water, and drying and fractionally distilling the organic phase.

If the isomeric 1-halogeno-2-methyl compounds have formed alongside the required products, they can be rearranged to the compounds I by treatment with acids, e.g. hydrogen chloride or hydrogen bromide, sulfuric acid or Lewis acids, at from $-50°$ to $+100°$ C.

The products I are valuable intermediates for the manufacture of scents and aromas of the type III

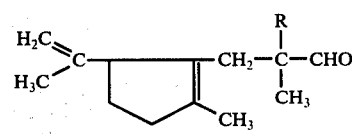   III where R is alkyl of 1 to 3 carbon atoms.

These compounds are obtained by reacting compound I with aldehydes IV

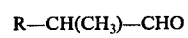   IV in the presence of bases. Since the halogen is in any case split off in this reaction, the chlorine derivative I is, economically, the most important halogen derivative. The bromine derivative only offers advantages for reaction with aldehydes IV of relatively low activity. The compounds III, and their derivatives with up to about six additional carbon atoms, which are obtained by acetalization or hydrogenation of the aldehyde group (the hydroxymethyl groups produced in the last-mentioned case may be esterified with lower fatty acids) are excellent scents for use in household preparations (detergents, washing-up liquids, cleansing agents and floor polishes) and cosmetics of all kinds. Furthermore, these scents are readily obtainable industrially via the intermediates according to the invention.

EXAMPLE 1

1-Methyl-2-chloromethyl-3-isopropenylcyclopent-1-ene 350 g (9.6 moles) of hydrogen chloride were passed, in the course of 6 hours, into a solution, at $-20°$ C, of 1,520 g (10 moles) of II and 1,500 ml of toluene, in which 50 g of copper powder were suspended. After separating off the copper, 20 g of potassium carbonate were added to the solution, the toluene was removed at 50 mm Hg and 60° C, and the product was distilled off the non-volatile constituents at 28°–42° C and 0.1 mm Hg. Fractionation of the distillate gave the desired product in 87% yield; boiling point 32° C/0.05 mm Hg; $n_D^{25} = 1.4928$.

EXAMPLE 2

1-Methyl-2-chloromethyl-3-isopropenylcyclopent-1-ene 530 g (5.5 moles) of phosgene were passed, in the course of 6 hours, into a solution of 760 g (5 moles) of II, 440 g of dimethylformamide and 2,000 ml of toluene at from 0° to +5° C. 1,000 ml of water were added to the solution and the aqueous phase was extracted twice with 100 ml of toluene at a time. The combined organic phases were washed first with sodium carbonate solution and then with water. On working up by distillation, the product was obtained in 78% yield.

EXAMPLE 3

1-Methyl-2-chloromethyl-3-isopropenylcyclopent-1-ene 24 g (0.2 mole) of thionyl chloride were added in the course of one hour to a solution of 31 g (0.2 mole) of II and 100 ml of toluene at room temperature. On working up by the method described in Example 2, the product was obtained in 90% yield.

EXAMPLE 4

1-Methyl-2-bromomethyl-3-isopropenylcyclopent-1-ene

A solution of 24 g (0.1 mole) of phosphorus tribromide and 30 ml of pentane was added, in the course of one hour, to a solution of 32 g (0.2 mole) of II, 80 ml of pentane and 4 ml of pyridine at −40° C. On working up by the method described in Example 2, the product was obtained in 81% yield; boiling point 40°–42° C/0.05 mm Hg; $n_D^{25} = 1.5064$.

We claim:

1. Cyclopentene derivatives of the general formula I

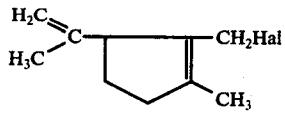

where Hal is chlorine, bromine or iodine.

2. A process for the manufacture of a cyclopentane derivative as claimed in claim 1, wherein 1-methyl-2-methylene-3-isopropenyl-cyclopentan-1-ol (II)

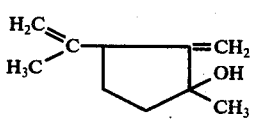

is reacted with a chlorinating, brominating or iodinating agent at from −50° to +100° C, said agent being selected from the group consisting of hydrogen chloride, hydrogen bromide, phosphorus trichloride, phosphorus pentachloride, thionyl chloride, phosphorus tribromide, phosphorus pentabromide, thionyl bromide, phosgene and hydrogen iodide.